United States Patent [19]

Takahashi et al.

[11] 3,989,600

[45] Nov. 2, 1976

[54] DISTILLING H₂O FROM AROMATIC CARBOXYLIC ACID AT A PH EXCEEDING 9

[75] Inventors: Satoshi Takahashi; Tomio Harada; Koshi Namie, all of Matsuyama; Hiroshi Shirahige, Ehime; Masayuki Sakurai, Matsuyama, all of Japan

[73] Assignee: Teijin Hercules Chemical Co., Ltd., Tokyo, Japan

[22] Filed: Dec. 23, 1974

[21] Appl. No.: 534,905

[30] Foreign Application Priority Data
Dec. 26, 1973 Japan.............................. 48-144039

[52] U.S. Cl. ................................ 203/15; 203/33; 203/36; 260/475 R; 260/525
[51] Int. Cl.² ............................................... B01D 3/00
[58] Field of Search .................. 203/10, 11, 14, 15, 203/16, 33, 36, 37; 260/475 R, 525; 23/230

[56] References Cited
UNITED STATES PATENTS

| | | | |
|---|---|---|---|
| 2,444,527 | 7/1948 | Pomeroy | 203/37 |
| 2,494,133 | 1/1950 | Jeffs | 203/33 |
| 2,508,911 | 5/1950 | Garner | 203/33 |
| 2,938,837 | 5/1960 | Meyer et al. | 203/33 |
| 3,047,612 | 7/1962 | Pennington et al. | 260/475 R |
| 3,432,399 | 3/1969 | Schutt | 203/11 |
| 3,558,277 | 1/1971 | Laman et al. | 23/23 |
| 3,890,374 | 6/1975 | Fujii | 260/475 R |

OTHER PUBLICATIONS

Parsons: *Chemical Treatment of Sewage & Industrial Wastes* pp. 33–47 relied upon.
Bochinski: *Pollution Engineering* 1/73 pp. 45 & 46.

*Primary Examiner*—Norman Yudkoff
*Assistant Examiner*—J. Sofer
*Attorney, Agent, or Firm*—Sherman & Shalloway

[57] ABSTRACT

A process for treating an aqueous solution containing organic compounds and having a high chemical oxygen demand (COD) by distilling the aqueous solution at a pH not lower than 9, and recovering the water of low chemical oxygen demand (COD) from said aqueous solution. The aqueous solution containing the organic compounds to be treated is derived from the reaction mixture of the oxidation system of methyl-substituted aromatic compound in the liquid phase with molecular oxygen or a molecular oxygen-containing gas, in the presence of a heavy metal catalyst but in the substantial absence of a lower aliphatic acid solvent, to form the corresponding aromatic acid.

10 Claims, No Drawings

DISTILLING H₂O FROM AROMATIC CARBOXYLIC ACID AT A PH EXCEEDING 9

This invention relates to a process for treating the containing organic compounds and having an aqueous solutions of high COD (Chemical Oxygen Demand) which are removed during the Process oxidizing of methyl-substituted aromatic compounds. More particularly, the invention relates to a process for treating the aqueous solutions organic compounds-containing of high COD which are separated from the reaction system in which methyl-substituted aromatic compounds, particularly p-xylene or mixtures of p-xylene with methyl p-toluate, are oxidized to form the corresponding aromatic carboxylic acids; and recovering the water of low COD.

Oxidation of methyl-substituted aromatic compounds in the presence of a heavy metal catalyst but in the substantial absence of lower aliphatic acid solvent, in the liquid phase, with molecular oxygen or a molecular oxygen-containing gas, to form the corresponding aromatic carboxylic acid is a widely practiced art, particularly for oxidizing p-xylene or mixtures of p-xylene and methyl p-toluate to form terephthalic acid or dimethyl terephthalate. In such oxidation reaction, for example, water is by-produced according to the formula below:

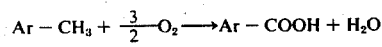

$$Ar - CH_3 + \frac{3}{2} O_2 \longrightarrow Ar - COOH + H_2O$$

in which Ar denotes an aromatic residue.

This water is separated from the reaction system as an aqueous solution of high COD, containing numbers of organic compounds. Normally, COD of the solution reaches as high as 20 – 200 g/l, when measured using potassium dichromate as described later, and the solution must be subjected to a COD-reducing treatment before being discarded.

The types of the organic compounds which cause the increase in COD differ somewhat, depending on the types of methyl-substituted aromatic compounds used as the starting material of the oxidation reaction, the heavy metal catalyst, and the method of separating the aqueous solution, etc., but in all cases the main component is formed of the low molecular weight by-products which are difficult to separate from water and are formed through the various side-reactions taking place in the oxidation of methyl-substituted aromatic compounds to form the corresponding aromatic carboxylic acids.

Accordingly, as the COD-reducing treatment, a simple distillation or solvent extraction of the solution may be conceived. However, heretofore it has been extremely difficult to satisfactorily reduce COD by such treatment, because (1) the COD contributing components are versatile, (2) the main components are either azeotropic with water, or have boiling points close to that of water, and consequently are difficultly separable from water, (3) the chemical structures of some of the COD-contributing components are not yet clear, and (4) no less than 99% of the organic compounds must be removed because of the extremely high COD. For these reasons such processes as the activated sludge process, combustion process, and the like, which are applicable also for treating the aqueous solutions containing miscellaneous components, have been employed.

When the activated sludge process is employed, however, a large aeration tank is necessary, and furthermore nutrients must be externally supplied, because phosphorus and nitrogen are not found in the specified aqueous solution. The solution must also be diluted with a large volume of water, because of the excessively high COD. Thus the maintenance and control of the activated sludge process create serious problems. In the combustion process, the whole aqueous solution is burnt in a high temperature furnace, to convert the organic compounds in the solution completely to harmless carbon dioxide and water. Because the greatest part of the aqueous solution is water however, the solution has no spontaneous combustibility and consequently requires a large quantity of heavy oil as fuel. Thus the process causes the problem of atmospheric pollution, and also is economically disadvantageous.

An object of the present invention, therefore, is to provide a process for treating the organic compounds containing aqueous solutions of high COD which are separated from the reaction systems for oxidizing methyl-substituted aromatic compounds to make the corresponding aromatic carboxylic acids, to thereby effectively and economically remove the organic compounds and allow the recovery of water of low COD.

According to our studies, it was discovered that the above object can be accomplished by distilling the organic compounds-containing aqueous solution of high COD, which is separated from the oxidizing system of methyl-substituted aromatic compound in the presence of a heavy metal catalyst but in the substantial absence of a lower aliphatic acid solvent, in the liquid phase, with molecular oxygen or a molecular oxygen-containing gas, to make the corresponding aromatic carboxylic acid, at a pH not lower than 9.

Specifically, the invention provides a process for treating an organic compounds-containing aqueous solution of high COD which is separated from the reaction system of oxidizing a methyl-substituted aromatic compound with molecular oxygen or a molecular oxygen-containing gas in the liquid phase, in the presence of a heavy metal catalyst but in the substantial absence of any lower aliphatic acid solvent, to form the corresponding aromatic carboxylic acid, which comprises distilling the organic compounds-containing aqueous solution at a pH not lower than 9, and recovering from said solution the water of low COD.

The term, "methyl-substituted aromatic compound", is used in this specification and the attached Claims to signify aromatic having at least one methyl group as a direct substituent in its aromatic ring. Examples of such compounds include benzene-type or naphthalene-type compounds having 1 – 3 methyl groups, such as toluene, xylene, trimethylbenzene, alkyl toluate, tolualdehyde, and methylnaphthalene. When those methyl-substituted aromatic compounds are oxidized with molecular oxygen or a molecular oxygen-containing gas in liquid phase, in the presence of the compounds of such metals as cobalt, manganese, nickel, and chromium (heavy metal catalyst), for example, cobalt acetate, manganese acetate, or the like, and in the substantial absence of lower aliphatic acid solvent such as acetic acid, propionic acid, and the like, the methyl group or groups are oxidized, and the corresponding aromatic carboxylic acid can be obtained. The expression "in the substantial absence of lower aliphatic acid solvent"

mentioned above means that no lower aliphatic acid is positively added to the reaction system, and it is not intended that the presence of a small quantity of lower aliphatic acids which are by-produced during the reaction should be eliminated.

The above-described oxidizing method is industrially widely practiced for the reaction as later described, particularly for the oxidation of mixture of p-xylene and methyl p-toluate, and of toluene.

The the preparation of dimethyl terephthalate from p-xylene according to the process known as the Witten process or Witten-Hercules process, has been industrially practiced on a large scale. According to said process, p-xylene is oxidized in the liquid phase with molecular oxygen or a molecular oxygen-containing gas in the presence of a heavy metal catalyst as already described, and in the substantial absence of lower aliphatic acid solvent, to be converted to p-toluic acid (first step), which is esterified with methanol to form methyl p-toluate (second step). The methyl p-toluate is again oxidized and converted to monomethyl terephthalate in a similar manner (third step), which is esterified with methanol to form the object dimethyl terephthalate (fourth step). Thus the process comprises four stages (see, for example, British patent specification No. 727,989). There has also been proposed an improvement of the above process, which comprises the two stages of oxidizing a mixture of p-xylene and methyl p-toluate, and esterifying the product with methanol, this improvement presently being adopted by the industries almost exclusively.

In this improved process, a mixture of p-xylene and methyl p-toluate is oxidized in the liquid phase with molecular oxygen or a molecular oxygen-containing gas, in the presence of a heavy metal catalyst as aforesaid, and in the substantial absence of a lower aliphatic acid solvent, to form a mixture of p-toluic acid and monomethyl terephthalate, which is esterified with methanol, and dimethyl terephthalate is separated from the esterified product. To the residue composed mainly of methyl p-toluate, fresh p-xylene is added, and again subjected to the oxidation, to provide a mixture of monomethyl terephthalate and p-toluic acid (see, for example, British patent specification No. 809,730). The obtained dimethyl terephthalate thus obtained is used mostly as the starting material in preparing polyesters.

When toluene is oxidized in a similar manner, benzoic acid is obtained. This process again is industrially practiced on huge scales. The benzoic acid formed is used as the starting material of ε-caprolactam, phenol, terephthalic acid, dyestuffs, and the like.

The oxidation of various methyl-substituted aromatic compounds as above-named is performed by feeding into a reactor the starting methyl-substituted aromatic compound and the catalyst such as a cobalt compound, or a mixture of that with a manganese compound, and blowing into the liquid starting material at a high temperature and elevated pressure either molecular oxygen or a molecular oxygen-containing gas.

In such an oxidation reaction, water is formed according to the reaction formula given in the early part of this specification. Water may also be used to dissolve the catalyst to be charged into the reactor. The water of such sources is separated from the reaction mixture by suitable means.

For instance, when the temperature and pressure of the oxidation are properly selected, the water is entrained by the molecular oxygen or the molecular oxygen-containing gas remaining after the reaction (waste gas), and discharged from the reactor. The waste gas occasionally contains, together with water, the starting methyl-substituted aromatic compound. Upon cooling the waste gas, therefore, the condensate is separated into two phases, the aromatic compound phase (organic phase) and aqueous phase. The two phases can be subsequently separated, the aromatic compound phase being recycled as the starting material of oxidation, and the aqueous phase being driven out of the system.

If an extremely high pressure is employed for the oxidation, or the oxidation is advanced while recycling into the reactor the whole condensate obtained upon cooling the waste gas, the water enters into the oxidation reaction mixture. If the reaction mixture forms an organic phase and an aqueous phase, the system can be separated to isolate water. When such two phases are not formed, the reaction mixture may be fractionated, for example, to allow separation of water as a fraction of the distillate.

In the oxidation of a methyl-substituted aromatic compound with molecular oxygen or a molecular oxygen-containing gas in the liquid phase, in the presence of a heavy metal catalyst and in the substantial absence of a lower aliphatic acid solvent, to form the corresponding aromatic carboxylic acid, various side-reactions take place besides the intended oxidation. As the resultant side-products, for example, formic acid, acetic acid, carbon monoxide, carbon dioxide, high boiling point tar-like substances, etc., are known, but besides the above-named, there are wide varieties of side-products of unknown structures, if barely traceable components also are taken into consideration. Of those side-products, the components which have properties resembling water composed mainly of formic acid and acetic acid, i.e., those having boiling points close to that of water, or which are azeotropic with water, or are extremely easily water-soluble, inavoidably enter into the aqueous phase or the water fraction of the distillate, during the afore-described water-separating procedures from the oxidation reaction mixture. The isolated aqueous phase or fraction of distillate furthermore, also contains minor amounts of other side-products, unreacted starting material, intermediate products, and the object product. In fact, therefore, the aqueous phase or the distillate is an aqueous solution containing many types of organic matter, and has a pH normally no higher than 4, in most cases below 3, and a COD as measured using potassium dichromate described later (hereinafter which may be abbreviated as COD-Cr) no less than 10 g/l, mostly no less than 50 g/l and below 400 g/l.

For example, when a mixture of p-xylene with methyl p-toluate is oxidized with air according to the aforesaid Witten-Hercules process, and the waste gas is driven out of the system from the top of the reactor, the waste gas contains, besides the non-condensing components such as nitrogen, a minor amount of oxygen, and carbon monoxide and dioxide by-produced in the oxidation, the following condensable components:
1. the water formed in the oxidation,
2. unreacted p-xylene,
3. wide varieties of side-products formed in the various side-reactions taking place during the oxidation of the mixture of p-xylene and methyl p-toluate (e.g., acetic acid, formic acid, and methanol, etc.)

4. unreacted methyl p-toluate
5. p-toluic acid which is the object product
6. various oxidation intermediate products
(e.g., p-tolualdehyde, p-methylbenzyl alcohol, etc.).

Of the above-named, quantitatively predominant components are (1) and (2) above, and when the waste gas is cooled to normal temperature, the condensable components take the liquid state, forming a p-xylene phase (organic phase) and an aqueous phase. The components (3) through (6) are distributed between the p-xylene phase and aqueous phase according to the distribution ratio unique for each of the components. The two phases are then separated. The p-xylene phase can be re-used as the starting material of the oxidation if necessary. The aqueous phase (aqueous solution), on the other hand, has a COD-Cr of normally 50 – 200 g/l, and if discarded as it is, inevitably causes the problem of environmental pollution.

The substances causing such a high COD are mainly the side-products classified under the group (3) above, while the unreacted starting materials, object product and oxidation intermediate products of the groups (2), (4), (5), and (6) also contribute to raise the COD by minor degrees. That is approximately 85% of the COD originates from acetic acid, formic acid, and methanol; approximately 5%, from p-xylene, methyl p-toluate, p-toluic acid, p-tolualdehyde, and p-methylbenzylalcohol (the compounds of the groups (2), (4), (5), and (6)). While the source of the remaining approximately 10% of COD is yet unclear, it is presumed that the wide variety of side-products of group (3), besides the named acetic acid, formic acid, and methanol, contribute to raise the COD of the solution.

Thus the COD-contributing components in the aqueous solution are extremely versatile, some having unknown structures. Even if a certain treatment is appropriate for removing 99% of COD-contributing components, if it is ineffective for the remaining 1%, the COD-Cr of the so-treated aqueous solution becomes still as high as approximately 500 – 2,000 ppm, which is objectionable from the standpoint of preventing environmental pollution.

Due to the foregoing reasons, it is extremely difficult to reduce COD of the solution by a simple treatment.

For instance, simple fractionation of the aqueous solution separated from the oxidation reaction mixture obtained in the aforesaid Witten-Hercules process only reduces the COD-Cr of the aqueous fraction of distillate to 10 – 100 g/l, a value apparently too high to allow discarding of the distillate as it is.

As already mentioned, we have now discovered that, upon distilling the organic compounds-containing aqueous solution of high COD as separated from the oxidation reaction mixture formed in the Witten-Hercules process, at a pH not lower than 9 in the manner of practice known per se, the COD of the resulting aqueous fraction of distillate can be reduced to such low level as 50 – 500 ppm, for example, and that said fraction is fit to be discarded as it is.

The foregoing explanations, particularly of the aqueous solution separated in the practice of the Witten-Hercules process, have been described in detail merely to facilitate the readers' understanding, and represent a preferred embodiment of the subject invention. It is understood that insofar as aqueous solution is that separated from the oxidation reaction system for oxidizing methyl-substituted aromatic compound in the liquid phase with molecular oxygen or a molecular oxygen-containing gas in the presence of a heavy metal catalyst but in the substantial absence of a lower aliphatic acid solvent to form the corresponding aromatic carboxylic acid, there is no drastic difference in the nature of the discharged organic compounds-containing aqueous solution regardless of the type of the starting methyl-substituted aromatic compound and the method of separating said aqueous solution. That is, the COD-contributing substances in the solution are mainly acetic acid and formic acid, although by less degree, other varieties of side-products which are formed by the various side-reactions taking place during the oxidation of methyl-substituted aromatic compound to form the corresponding aromatic carboxylic acid, and which are difficult to be separated from water contribute to the COD. The nature of such aqueous solution is substantially the same with that of the aqueous solution separated from the reaction mixture formed according to the Witten Hercules process, and the foregoing explanations on the latter solution are perfectly applicable also to the former.

Accordingly, it should be understood that the process of this invention is applicable not only to the organic compounds-containing aqueous solution separated from Witten Hercules process, but also to any organic compounds-containing aqueous solution separated from the oxidation reaction mixture of the system for oxidizing methyl-substituted aromatic compound in the liquid phase with molecular oxygen or a molecular oxygen-containing gas, in the presence of a heavy metal catalyst but in the substantial absence of a lower aliphatic acid solvent, to form the corresponding aromatic carboxylic acid, in entirely the same manner.

The treatment of this invention is equally applicable, as aforesaid, to any organic compounds-containing aqueous solution separated from an oxidation reaction mixture, regardless of the method of separating the solution employed, but it is particularly effective when applied to the aqueous solution separated from the reaction system in which a mixture of p-xylene and methyl p-toluate, or toluene, is oxidized particularly by the aforedescribed Witten-Hercules process.

The subject process may be directly applied to the aqueous solution as separated, or to the solution from which the COD-contributing components which are easily separable through simple procedures such as distillation or solvent extraction have been removed in advance. For example, the aqueous solution separated from the oxidation system in accordance with the Witten process contains a minor amount of methanol, as aforesaid, which can be separated from water by distillation with relative ease. Therefore, the methanol may be removed by a preliminary distillation preceding the treatment of this invention, or recovered as the initial fraction of distillate in the later-described distillation procedure according to the invention.

Furthermore, the subject process may be applied to the aqueous solution alone, or to the mixture thereof with other waste water, such as the water discharged from the esterifying step.

According to the invention, the pH of the aqueous solution separated as above is adjusted to not lower than 9, preferably not lower than 10, in advance of the distillation.

The pH-adjustment can be easily effected by adding to the solution a substance which exhibits basic property in the same solution (which will be hereinafter referred to as "the basic substance"). The type of the basic substance is not critical so far as it is capable of raising the pH of the solution to above 9, but particularly basic alkali metal compounds, alkaline earth metal compounds, or the substances which can form such metal compounds in the aqueous solution, are conveniently used.

As the basic alkali metal compounds or alkaline earth metal compounds, hydroxides and carbonates of alkali metals and alkaline earth metals, such as sodium hydroxide, potassium hydroxide, lithium hydroxide, calcium hydroxide, barium hydroxide, sodium carbonate, potassium carbonate, and the like, are preferred.

Again, examples of the substances which can form the basic alkali metal compounds or alkaline earth metal compounds in the aqueous solution include the metals and metal oxides such as metal sodium, metal calcium, sodium oxide, potassium oxide, and calcium oxide.

These basic substances may be used singly, or two or more of them may be concurrently used.

Of the above-named, those particularly preferred are calcium oxide, calcium hydroxide, and sodium hydroxide, all of which are inexpensive and easy to handle.

Those basic substances may be added to the solution to be treated as they are, or in the form of aqueous solution or the like.

According to the invention, the basic substance is added to raise the pH of the aqueous solution to be treated to not lower than 9, preferably above 10, more preferably, not lower than 11.

It has also been discovered that, particularly when calcium metal or a calcium compound is used as the basic substance to raise the pH to 10 or above, scaling or foaming in the evaportor can be substantially eliminated.

When the aqueous solution having a pH lower than 9 is distilled, the resulting aqueous fraction of distillate shows a considerably reduced COD, but not as low as will allow the discarding of the distillate as it is.

According to the invention, the aqueous solution may be distilled immediately after its pH has been adjusted, but we discovered that the water of still further reduced COD can be recovered if the solution whose pH has been adjusted by the addition of basic substance is either heated at a pH of not lower than 9, or stored at room temperature, and thereafter distilled.

This effect is particularly conspicuous when the solution is heated before the distillation.

This heating treatment comprises heating the aqueous solution whose pH has been adjusted to not lower than 9, to at the lowest 60° C., preferably to a temperature not lower than 80° C. While there is no critical upper limit to the heating temperature, excessively high temperature heating fails to show any justifying additional effect, and therefore it is normally sufficient to employ the temperature up to 120° C.

The heating time is variable over a wide range depending on such factors as the heating temperature, types and concentrations of the organic compounds in the aqueous solution, but normally it should be not shorter than 5 minutes. Again there is no critical upper limit, but prolonged heating is wasteful from the viewpoint of thermal economy, because no notable additional effect is thereby obtained. Accordingly, normally it is sufficient to continue the heating for up to an hour. For instance, it is normally appropriate to effect the heating at 60° C. or above for at least 5 minutes, preferably at 80° C. or above for no shorter than 10 minutes.

Quite satisfactory results can be obtained by for 10 to 30 minutes heating for 10 to 30 minutes at 80° – 100° C.

The above-described heating treatment may be effected in combination with the later-specified distillation. In that case, a temperature not lower than 60° C. is employed, and the distillation conditions are so selected to secure sufficiently long staying time of the solution in the evaporator, whereby the separate heating treatment may be omitted.

Instead of the heating, the aqueous solution having the adjusted pH of not lower than 9 may be stored for a long time at room temperature, and then distilled. The storing time is normally no shorter than 10 hours, and no shorter than one day for obtaining satisfactory results.

Upon addition of the basic substance to the aqueous solution according to the invention, the formic acid and acetic acid present in the solution are neutralized to form the salts of the alkali metal or alkaline earth metal. Although formic acid and acetic acid are themselves difficult to be separated from water by distillation, the salts thereof are non-volatile, and can be readily separated as the residue. However, the action of the basic substance according to the invention is by no means limited to the neutralization of organic acids. Since, if the action of the basic substance is no more than simple neutralization, the necessity of raising the pH to not lower than 9, preferably, 10, and the improving effect of heating or storing, cannot be explained.

As already mentioned, the aqueous solution contains versatile organic compounds, some of which are difficult to separate from water by distillation, like formic acid and acetic acid, which presumably are converted to forms which are easily separable from water, or to substances which do not substantially contribute to raise the COD, by the special action of the basic substance.

According to the invention, after the addition of basic substance, the aqueous solution heated as above or stored is distilled, and separated into the distilled water of low COD and the residue in which the COD-contributing organic components and the basic substance are concentrated. This distillation can be practiced according to accepted practice. For example, the pressure may be normal or reduced, and the distillation may be carried out either continuously or batchwise, until suitably the solid concentration in the residue reaches 20 – 70% by weight, preferably 30 – 50% by weight, from the standpoints of easy handling and reasonable treating cost. If the distillation is advanced to a higher concentration than the above upper limit, the liquid's viscosity rises abruptly, causing vigorous foaming and scaling trouble. Particularly when the solid concentration exceeds 70%, the system causes gelation, and frequently invites such troubles as clogging of the pipes, damaging the equipment, and the like. The solid matter in the distillation residue is self-combustible containing 70 – 80% thereof of organic matter (2,000 – 3,000 Kcal/kg), and can be burnt as in the liquid or after being spray-dried, in an incinerator or rotary kiln at 700° C. or above. For example, by burning the residue at 900° C. for no shorter than 15 minutes, the organic component is almost completely decomposed to harmless $H_2O$ and $CO_2$, and the inorganic component becomes the combustion residue.

According to our studies, this combustion residue can be re-used as the basic substance useful for the subject process. To wit, the basic substance thus can be recycled in the subject process, and therefore its consumption is extremely low in treating large quantities of the aqueous solution. This also is one of the most characteristic features of this invention.

Particularly when calcium metal or a calcium compound is used as the basic substance, the wear of the construction material of the incinerator or rotary kiln is very little. Therefore it is recommended to use calcium metal or a calcium compound as the pH-regulating agent according to the invention, if the basic substance is to be recirculatively used.

The water recovered from the treating system according to the subject process has drastically reduced COD compared with that of the aqueous solution before the treatment, and can be discarded as it is without causing the problem of environmental pollution, although it may be further treated to have still reduced COD if so desired. In the further treatment, the feedwater gives markedly light load on the treating process, because its COD itself is satisfactorily low.

As mentioned in the beginning, the term, "COD", used in this specification is the abbreviation of Chemical Oxygen Demand, signifying the amount of oxygen consumed by the oxidized substance in water, mainly organic matters. The numerical values of COD shown in the following Examples are those determined by the measuring method disclosed in Japanese Industrial Standard (JIS) K-0102 (1971), "Industrial Waste Water Testing Method", indicated by g/liter and ppm.

In particular, "COD-Cr" signifies the oxygen demand of potassium dichromate, which is determined by the steps of adding to the test body a predetermined amount of potassium dichromate solution, sulfuric acid-silver sulfate solution and mercuric sulfate, boiling the system for 2 hours under reflux to cause the reaction, and titrating the excessive potassium dichromate with ammonium ferrous sulfate solution to determine the potassium dichromate consumption, from which its oxygen demand is calculated. [ASTM, D 1252-60 Chemical Oxygen Demand (Dichromate Oxygen Demand) of industrial waste water.]

Whereas, "COD-Mn" signifies the oxygen demand of potassium permanganate at 100° C. To the test body each predetermined amount of sulfuric acid, silver sulfate, and potassium permanganate solution are added, and reacted in boiling water for 30 minutes. To the excessive potassium permanganate, a predetermined amount of sodium oxalate is added and back titrated with the potassium permanganate solution. The oxygen demand is calculated from the determined potassium permanganate consumption.

Hereinafter the invention will be more specifically explained with reference to the working examples, it being understood that the scope of this invention is in no way limited thereby.

EXAMPLE 1

A bubble tower-type oxidation reactor was charged with a mixture of p-xylene and methyl p-toluate as the starting material, and a mixture of cobalt acetate and manganese acetate as the catalyst, and air was blown into the bubble tower from the bottom, at a temperature of 168° C. and a pressure of 3.9 kg/cm$^2$G, to continuously produce a mixture of p-toluic acid and monomethyl terephthalate by oxidation reaction. The air remaining after the oxidation reaction (waste gas) was led out of the system through the top of the bubble tower, and cooled to 40° C. to cause condensation of the condensable components in the waste gas. The liquid condensate formed had an upper layer composed chiefly of p-xylene and a lower layer composed chiefly of water. The two layers were then separated, and the aqueous solution (the lower layer) was recovered.

The aqueous solution had a COD-Cr of 123 g/l, COD-Mn of 23.2 g/l, and pH of 1.9. The organic compounds contained in the aqueous solution were determined by means of gas chromatography, and COD-Cr's by each of the compounds were calculated to examine their contributions, with the results as shown in Table 1 below. The sources of 85% of the solution's COD-Cr of 123 g/l could be confirmed in this manner, but those of the remaining 15% were left unclear.

Table 1

| Component | Content (wt %) | Theoretical COD-Cr (g/l) | Contribution (%) |
|---|---|---|---|
| Formic acid | 1.62 | 5.5 | 4.5 |
| Acetic acid | 5.75 | 58.1 | 47.2 |
| Methanol | 2.79 | 39.9 | 32.4 |
| p-Xylene | 0.11 | 0.6 | 0.5 |
| Total | 10.27 | 104.1 | 84.6 |

To one liter each of this aqueous solution, respectively hydroxide of calcium, sodium, and barium was added to raise the former's pH to 11 or higher at room temperature. Each sample was divided into three groups A, B, and C. The A groups were boiled under reflux for 30 minutes and thereafter distilled. The B groups were immediately subjected to a reduced pressure distillation (the boiling point — not higher than 30° C.). The C groups were allowed to stand for a day and night at room temperature, and then distilled under reduced pressure (the boiling point — not higher than 30° C.). In all of the distillation systems, first the initial fraction of high COD was separated, and approximately 250 ml of aqueous distillate was collected as the main fraction. The results of measuring COD-Cr of the main fractions were as shown in Table 2 below.

Table 2

| Basic Substance | Treating Method | COD-Cr (g/l) |
|---|---|---|
| Ca(OH)$_2$ | A | 0.37 |
|  | B | 0.80 |
|  | C | 0.26 |
| NaOH | A | 0.26 |
|  | B | 1.60 |
|  | C | 0.33 |
| Ba(OH)$_2$ | A | 0.12 |
|  | B | 1.20 |
|  | C | 0.35 |

The distillation residue of the sample which pH had been adjusted with calcium hydroxide and which had been treated by method A was withdrawn and removed of water by heating, leaving a solid matter containing approximately 25% of Ca. By calcining the solid matter in an electric muffle furnace at 1000° C. for 15 minutes, a white ash of 65% Ca content (combustion residue) was obtained.

EXAMPLE 2

The aqueous solution which was the object of the treatment of Example 1 was distilled in a laboratory high efficient distillation apparatus, until the methanol content in the distillate was reduced no more than 0.01%, to distil off the low-boiling-point organic compounds such as methanol. Thus the distillation residue amounting to approximately 70% of the starting aqueous solution was obtained, which had a COD-Cr of 86 g/l, and COD-Mn of 9.4 g/l.

To each 500 ml of the distillation residue, respectively calcium hydroxide, calcium oxide, and the combustion residue obtained in Example 1 were added, to make the pH of all the systems 12.5 at room temperature.

Each system was boiled under reflux for 15 minutes. and subjected to simple distillation in a Vigreux column. The results of measuring COD-Cr (ppm) and COD-Mn (ppm) of each 100 ml of the fractions of distillate were as shown in Table 3 below.

Table 3

| Basic Substance | Ca(OH)$_2$ | | CaO | | Combustion Residue | |
|---|---|---|---|---|---|---|
| Fraction of Distillate | COD-Cr | COD-Mn | COD-Cr | COD-Mn | COD-CR | COD-Mn |
| 0 – 50 | 3640 | 1030 | 3290 | 1410 | 3360 | 1300 |
| 51 – 150 | 260 | 55 | 320 | 130 | 720 | 170 |
| 151 – 250 | 190 | 40 | 95 | 30 | 120 | 35 |
| 251 – 350 | 170 | 40 | 85 | 30 | 80 | 30 |
| about 351 – 420 | 100 | 30 | 85 | 25 | 60 | 15 |

EXAMPLE 3

To each 500 ml of the aqueous solution identical with that employed as the object of treatment of Example 2 (COD-Cr 108 g/l, pH, 2.0), granular sodium hydroxide (NaOH) was added, and pH of the systems were adjusted to the values indicated in Table 4, followed by boiling for 30 minutes under reflux. Each system was then subjected to simple distillation in a Vigreux Column and each 100 ml of the fractions of distillate were taken. The results of measuring COD-Cr(ppm) of the fractions are shown in Table 4.

Table 4

| | Fraction of Distillate | COD-Cr (ppm) | | |
|---|---|---|---|---|
| pH | 0–100 ml | 101–200 ml | 201–300 ml | 301–400 ml |
| no alkali added | 139000 | 98000 | 82000 | 32000 |
| pH 5 | 109000 | 75000 | 71000 | 32000 |
| 8.5 | 121000 | 5900 | 9900 | 1200 |
| 10 | 8700 | 4700 | 900 | 2000 |
| 11.5 | 2500 | 360 | 20 | 60 |
| 13 | 2800 | 600 | 80 | 90 |

EXAMPLE 4

Into a 500 ml stainless steel autoclave equipped with a reflux condenser, a stirrer and a gas inlet which was charged with 60 g of p-xylene, 140 g of methyl p-toluate, 5 g of p-toluic acid, and 500 mg of cobalt acetate, and air was blown at a pressure of 6 kg/cm$^2$G, a temperature of 150° C., under high-speed stirring, at such a rate as will make the flow rate at the exit 1000 ml/min. The reaction was continued for 3 hours.

Thereafter the content of the autoclave was cooled, and the oxidation reaction mixture was withdrawn.

The above oxidation was repeated 5 times, and the five batches of the reaction mixtures were combined, distilled, and separated, to provide approximately 50 ml of an aqueous solution. The solution had a COD-Cr of 166 g/l, and pH of 1.9

The solution was transferred into a 100 ml semi-micro distillator, and into which 40% aqueous NaOH was dropped to raise the former's pH to 13. After the subsequent 30 minutes' boiling under reflux (COD-Cr, 113 g/l), the system was distilled in Widmer Column. After removing 15 ml of initial fraction of distillate, the following 20 ml of aqueous distillate was collected, which had a COD-Cr of 740 ppm.

EXAMPLE 5

The oxidation of p-xylene and methyl p-toluate ws performed similarly to Example 1, and the waste gas was cooled to provide a liquid condensate (1).

Because the waste gas still contained minor amounts of the organic compounds, it was adsorbed onto activated carbon, and desorbed with steam. By cooling the same, another liquid condensate (2) was obtained.

On the other hand, the oxidation reaction mixture contained a minor amount of unreacted p-xylene, which was steam-distilled. The liquid condensate (3) obtained by cooling the distillate contained water, p-xylene, etc.

The three condensates were collected and mixed, and then left standing. There formed an upper layer composed mainly of p-xylene and a lower layer composed mainly of water which were separated, and the aqueous phase was sent to a flexy-tray type distillation column. Into the column 1 kg/cm$^2$G steam was blown so as to maintain the bottom temperature at 105° C., and the distilled methanol was recovered.

The waste water discharged from the bottom of the column was an aqueous solution of pH 2.4, having the COD-Cr of 21.6 g/l, and the odour of acetic acid.

To each 1 liter of this aqueous solution, hydroxides of respectively calcium, sodium, barium, and potassium was added to raise the pH to 10 or above, and each system was divided into two groups, A and B. The A groups were boiled for 10 minutes under reflux and then distilled, and the B groups were left standing for 30 minutes and then distilled under a reduced pressure (boiling point not higher than 40° C.).

In all runs of the distillation, the distillate was divided into the initial fraction 20%, main fraction (aqueous fraction of distillate) 60%, and the residue, 20%. Thereafter the COD-Cr of the initial fraction and of the main fraction were measured, with the result as shown in Table 6 below.

Table 6

| | | COD-Cr (ppm) | |
|---|---|---|---|
| Basic Substance | Method of Treating | Initial Fraction | Main Fraction |
| Ca(OH)$_2$ | A | 4000 | 200 |

Table 6-continued

| Basic Substance | Method of Treating | COD-Cr (ppm) Initial Fraction | COD-Cr (ppm) Main Fraction |
|---|---|---|---|
| NaOH | B | 1300 | 840 |
| | A | 4000 | 200 |
| Ba(OH)₂ | B | 2700 | 3800 |
| | A | 2500 | 300 |
| KOH | B | 1600 | 1700 |
| | A | 3200 | 550 |
| | B | 1900 | 3500 |

EXAMPLE 6

To 1,000 ml of the identical aqueous solution with that treated in Example 5 (COD-Cr, 19.0 g/l, COD-Mn, 2.3 g/l, pH 2.9), sodium carbonate was added to make the solution's pH 10.1.

After approximately 10 minutes' boiling under reflux, the system was distilled with a 30 cm long Vigreux Column and the distillate was divided into the initial fraction (0 – 100 ml of the distillate), main fraction (101 – 800 ml of the distillate), and last fraction (801 – 900 ml of the distillate).

The COD-Cr and COD-Mn of each fraction were measured with the results as shown in Table 7.

Table 7

| | COD-Cr (ppm) | COD-Mn (ppm) |
|---|---|---|
| Initial Fraction | 2400 | 1400 |
| Main Fraction | 140 | 40 |
| Last Fraction | 160 | 33 |

When sodium metal was used as the basic substance to make the solution's pH 12.3, the COD's of the main fraction of distillate obtained through the similar treatment were as follows:

| COD-Cr | 110 ppm |
|---|---|
| COD-Mn | 29 ppm |

EXAMPLE 7

A 500-ml stainless steel autoclave equipped with a reflux condenser, a stirrer and a gas inlet was charged with 200 g of toluene, 5 g of benzoic acid, 1 g of benzaldehyde, and cobalt acetate of the amount calculated to make the catalyst's (cobalt's) concentration in the starting material 300 ppm. Under the pressure of 10 kg/cm²G and at the temperature of 180° C., air was blown into the autoclave at such a rate as will make the flow rate of the gas at the exit 1000 ml/min., under high-speed stirring. After the oxygen absorption started, the reaction was continued for 3 hours.

The above experiment of oxidation was repeated 8 times, and the reaction mixtures of all runs were combined, distilled, and separated, to provide approximately 100 ml of an aqueous solution containing the various organic compounds, which had a COD-Cr of 38 g/l, COD-Mn of 3.9 g/l, and pH of 3.2. The organic compounds in the aqueous solution were determined by means of gas chromatography, and contributions of each component to the COD were calculated similarly to Example 1. The results were as shown in Table 8 below.

Table 8

| Component | Content (wt %) | Calculated COD COD-Cr (g/l) | Calculated COD COD-Mn (g/l) |
|---|---|---|---|
| Formic acid | 0.93 | 3.2 | 0.46 |
| Acetic acid | 1.71 | 17.3 | 1.35 |
| Toluene | 0.11 | 0.7 | 1.10 |
| Total | 2.75 | 21.2 | 2.91 |

Thus 56% of the COD-Cr and 75% of the COD-Mn could be explained away, but the sources of the rest of COD's could not be identified.

To this aqueous solution, 40% aqueous NaOH was added dropwise, to raise the solution's pH 12.9. Then the solution was boiled under reflex for 30 minutes (COD-Cr, 23 g/l), transferred into a 100 ml semi-micro distillation apparatus, and distilled with a 15 cm long Widmer Column attached thereto.

As the initial fraction of distillate, 20 ml was separated, and subsequently distilled 40 ml was collected as the aqueous fraction of distillate, which had a COD-Cr of 210 ppm and COD-Mn of 50 ppm.

We claim:

1. In the process for preparing an aromatic carboxylic acid selected from benzoic acid, p-toluic acid or a mixture of p-toluic acid with monomethyl terephthalate by the liquid phase oxidation of a methyl-substituted aromatic compound selected from toluene, p-xylene or a mixture of p-xylene with methyl p-toluate with molecular oxygen or a molecular oxygen containing gas in the presence of a heavy metal catalyst whereby condensation of the waste gas from said oxidation reaction results in an organic phase and an aqueous phase containing organic compounds and having a high chemical oxygen demand, a process for treating said organic compounds-containing aqueous phase of high chemical oxygen demand after being separated from said organic phase to lower the chemical oxygen demand of said aqueous phase which comprises distilling the organic compounds-containing aqueous phase at a pH not lower than 9, and recovering distilled water of lower chemical oxygen demand.

2. The process of claim 1, in which the organic compounds-containing aqueous phase is distilled at a pH not lower than 10.

3. The process of claim 1 wherein said aromatic carboxylic acid is benzoic acid and said aromatic compound is toluene.

4. The process of claim 1 wherein said aromatic acid is p-toluic acid and said aromatic compound is p-xylene.

5. The process of claim 1 wherein said aromatic acid is a mixture of p-toluic acid with monomethyl terephthalate and said aromatic compound is a mixture of p-xylene with methyl-p-toluate.

6. The process according to claim 1, in which the organic compounds-containing aqueous phase is heated at a pH not lower than 9, in advance of the distillation.

7. The process according to claim 6, in which the organic compounds-containing aqueous phase is heated to a temperature not lower than 60° C.

8. The process according to claim 1, which comprises distilling the organic compounds-containing aqueous phase in the presence of a metal compound selected from the group consisting of basic alkali metal compounds and alkaline earth metal compounds.

9. The process according to claim 8, in which the metal compound is hydroxide or carbonate.

10. The process of claim 9 wherein said metal compound is calcium hydroxide or calcium carbonate.

* * * * *